United States Patent
Carroll et al.

(10) Patent No.: US 7,129,479 B2
(45) Date of Patent: Oct. 31, 2006

(54) METHOD AND SYSTEM FOR INTRODUCING AN ANALYTE INTO AN ION MOBILITY SPECTROMETER

(75) Inventors: John J. Carroll, Madison, NJ (US); Reno Francis Debono, Annandale, NJ (US); Tri Le, Stroudsburg, PA (US); Robert Bruce Sandor, South Orange, NJ (US); Sabatino Nacson, Thornhill (CA); Alexander Grigoriev, Mississauga (CA)

(73) Assignee: Smiths Detection Inc. - Toronto, Mississauga (CA)

( * ) Notice: Subject to any disclaimer, the term of this patent is extended or adjusted under 35 U.S.C. 154(b) by 173 days.

(21) Appl. No.: 10/961,612

(22) Filed: Oct. 8, 2004

(65) Prior Publication Data

US 2005/0127286 A1    Jun. 16, 2005

Related U.S. Application Data

(60) Provisional application No. 60/509,754, filed on Oct. 8, 2003.

(51) Int. Cl.
   *B01D 59/44*    (2006.01)
(52) U.S. Cl. .................. 250/287; 250/281; 250/282
(58) Field of Classification Search .............. 250/287
   See application file for complete search history.

*Primary Examiner*—Nikita Wells
*Assistant Examiner*—Phillip A Johnston
(74) *Attorney, Agent, or Firm*—Foley & Lardner LLP

(57) ABSTRACT

A system and method for introducing and analyzing a sample containing an analyte using an ion mobility spectrometer are described. The system includes a temperature module for adjusting the temperature of the sample according to temperature instructions received, and a split ratio module for adjusting the split ratio according to split ratio instructions received. An ion mobility analyzer determines an ion mobility of the analyte. The ion mobility analyzer collects a plasmagram of the analyte to identify and quantitate the analyte.

35 Claims, 5 Drawing Sheets

METHOD AND SYSTEM FOR INTRODUCING AN ANALYTE INTO AN ION MOBILITY SPECTROMETER

FIELD OF THE INVENTION

The invention relates to quantitative analysis using ion mobility spectrometry, and more specifically to the introduction of a thermally evaporated sample in an ion mobility spectrometer.

BACKGROUND OF THE INVENTION

A fast method for analyzing samples in the pharmaceutical industry is ion mobility spectrometry, an analytical technique that characterizes chemical substances based on their gas-phase ion mobilities. These mobilities are determined by measuring drift velocities as ions move, under the influence of an electric field, through a gas at ambient pressure. The method can be up to two orders of magnitude faster and can be much cheaper than other methods, such as liquid chromatography (LC). Moreover, unlike LC, ion mobility spectrometry does not require highly trained personnel to administer the test.

In ion mobility spectrometry, an analyte, such as a pharmaceutical compound, is ionized and then inserted into a drift tube. The ions migrate downfield and strike a collector electrode, producing a current. The ion current is amplified and displayed as an ion mobility spectrum or plasmagram, showing ion current versus time. Such a plasmagram can be used to characterize the pharmaceutical compound.

Ion mobility spectrometry, therefore, involves two major steps: in the first step, a sample is prepared and inserted into the analyzer, and in the second step, the sample is analyzed. While some variations in the second step exist, not too many options are available for preparing and inserting the sample for analysis.

Often, the introduction step involves the use of a solution of analyte in a solvent. Unfortunately, the presence of solvents during the analysis stage can yield poor reproducibility and spurious plasmagrams. Therefore, any different method that could improve the introduction step, by increasing reproducibility, by increasing the number of solvents that can be used for analysis, or by allowing greater variability in sample size, would be most welcome.

SUMMARY OF THE INVENTION

A system and method for introducing and analyzing a sample containing an analyte with an ion mobility analyzer is described. A variable temperature vaporizer (VTV) is used to introduce the sample into the ion mobility analyzer. In one embodiment using VTV, the liquid sample is injected with the VTV temperature below the boiling point of the solvent, the sample is evaporated under a flow of gas to vent the solvent, and then the temperature is raised rapidly to vaporize the analyte.

Using VTV results in more reproducible results and also permits a larger number of solvents to be employed. As a consequence of the larger number of solvents that can be used, a wider range of analytes can be effectively characterized using ion mobility spectrometry.

In particular, an ion mobility spectrometer for characterizing a sample containing an analyte and possibly a solvent therefor is described below. The ion mobility spectrometer includes a vent-containing sample unit for holding the sample. The ion mobility spectrometer further includes a temperature module for adjusting the temperature of the sample unit according to temperature instructions received, and a split ratio module for adjusting split ratio according to split ratio instructions received. The split ratio is characteristic of the ratio of the flow rate of gas discharged through the vent to the flow rate of gas being delivered to the ion mobility analyzer from the sample unit. The ion mobility spectrometer further includes an ion mobility analyzer for determining an ion mobility of the analyte received from the sample unit, and a connector device for connecting and transferring the analyte from the sample unit to the ion mobility analyzer. The ion mobility can be used to characterize the sample. Because the foregoing system allows for venting of solvent, larger sample volumes can be used. Moreover, the use of the split ratio module can extend the dynamic range of the instrument.

Also described herein is a method for analyzing with an ion mobility analyzer a sample containing N analyte components, $\{C_1, C_2, \ldots, C_N\}$, where N is an integer greater than one, component $C_i$ has a lower desorption temperature than $c_j$ if i<j, and the desorption temperature of the solvent is less than the desorption temperature of $c_1$. The method includes holding the sample in a sample unit, and adjusting the temperature of the sample unit to at least the desorption temperature of the solvent to allow desorption thereof. The method further includes adjusting the temperature of the sample unit to at least that of the desorption temperature of $c_1$, to allow desorption thereof, and transferring $c_1$, from the sample unit to the ion mobility analyzer for analysis. Further, the method includes adjusting the temperature of the sample unit to at least that of the desorption temperature of $c_2$ to allow desorption thereof, and transferring $c_2$ from the sample unit to the ion mobility analyzer for analysis. Where N>2, the steps of adjusting and transferring are repeated until all N components are sent to the ion mobility analyzer. The split ratio of at least one member of the group consisting of the solvent and the N components may be adjusted, according to split ratio instructions received by a split ratio module.

BRIEF DESCRIPTION OF THE DRAWINGS

For a better understanding of the present invention and to show more clearly how it may be carried into effect, reference will now be made, by way of example, to the accompanying drawings, in which.

DETAILED DESCRIPTION OF THE INVENTION

Figure 1:
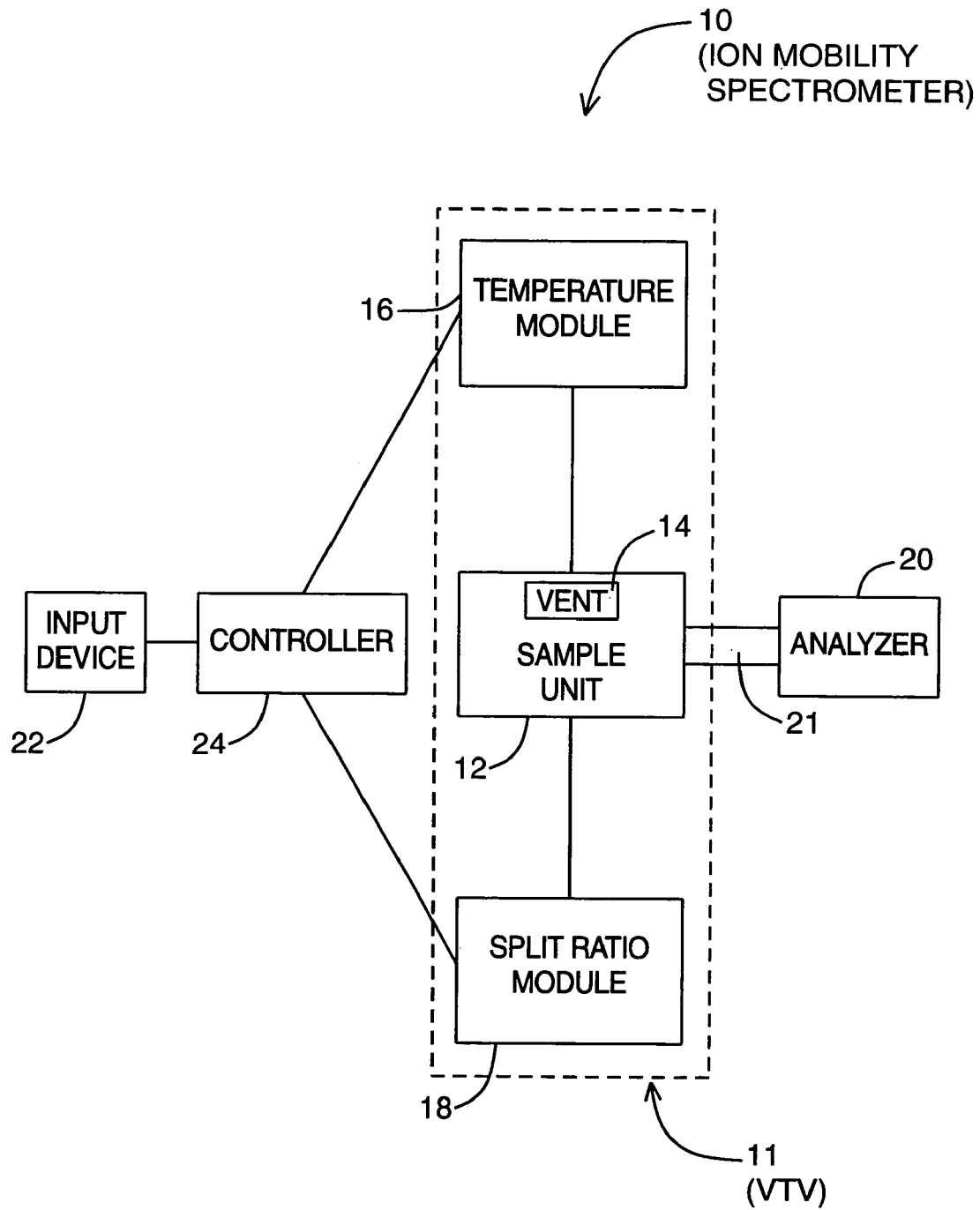
FIG. 1 shows a block diagram of an ion mobility spectrometer for characterizing an analyte.

FIG. 1 shows a block diagram of an ion mobility spectrometer 10 for characterizing an analyte. The ion mobility spectrometer 10 includes a programmable temperature vaporizer 11 that contains a sample unit 12 having a vent 14. The ion mobility spectrometer 10 also includes a temperature module 16, a split ratio module 18, an ion mobility analyzer 20, and a connector device 21. The ion mobility spectrometer 10 can further include an input device 22 and/or a controller 24.

The sample unit 12 holds a sample containing the analyte and a solvent. The analyte can be dissolved in appropriate solvents, which can be vented through the vent 14 to reduce the volume of the solvent. As discussed in more detail below, the amount of solvent vented is determined by the split ratio, which is characteristic of the ratio of the flow rate of gas discharged through the vent 14 to the flow rate of gas being delivered to the ion mobility analyzer 20 from the sample unit 12.

The temperature module 16 adjusts the temperature of the sample unit 12 according to temperature instructions received. These temperature instructions can be determined and sent by the controller 24 to the temperature module 16. The controller 24 determines these instructions based on the physical characteristics of the sample, which characteristics can be input by a user via the input device 22, such as a keyboard connected to a computer. Alternatively, the temperature instructions can be input by the user using the input device 22. The controller 24 can process the temperature instructions and can then send corresponding control signals to the temperature module 16.

The split ratio module 18 adjusts the split ratio according to split ratio instructions received. The split ratio instructions can be determined and sent by the controller 24 to the split ratio module 18. The controller 24 determines these instructions based on the physical characteristics of the sample, which characteristics can be input by a user via the input device 22. Alternatively, the split ratio instructions can be input by the user using the input device 22. The controller 24 can process the split ratio instructions and can then send corresponding control signals to the split ratio module 18.

The ion mobility analyzer 20 determines the ion mobility of the analyte received from the sample unit 12. The connector device 21 connects and transfers the analyte from the sample unit 12 to the ion mobility analyzer 21. The ion mobility obtained therefrom can be used to characterize the analyte.

In one embodiment, the controller 24 determines the temperature instructions and the split ratio instructions based on physical characteristics of the solvent and the analyte. Typically, the physical characteristics used by the controller 24 to determine the temperature and split ratio instructions include the boiling points and masses of the solvent and the analyte. Alternatively, the appropriate temperatures and/or split ratios can be entered directly via an input device 22 by a user.

Figure 2:
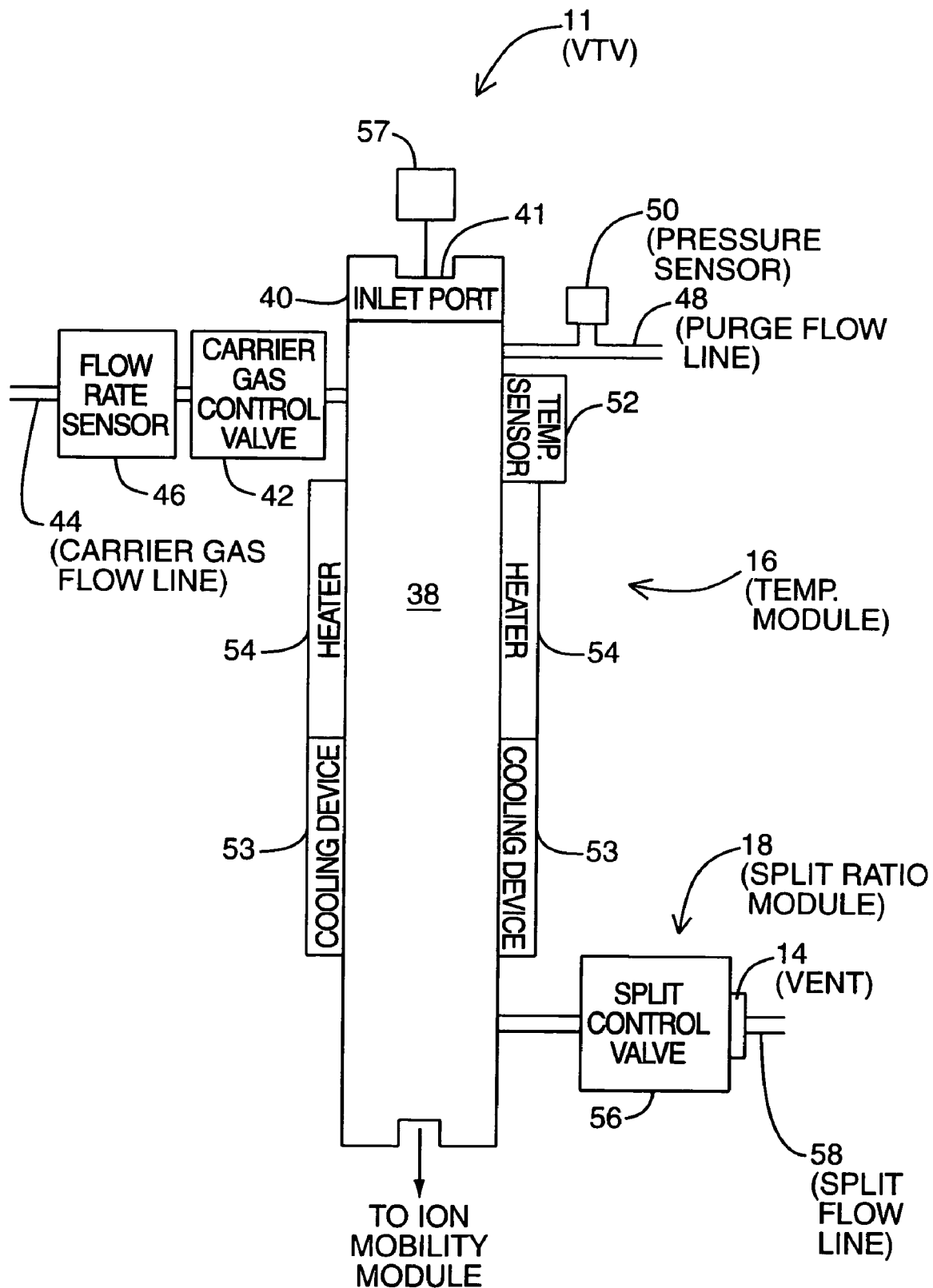
FIG. 2 shows a schematic diagram of the programmable temperature vaporizer of FIG. 1.

FIG. 2 shows a schematic diagram of the programmable temperature vaporizer 11 of FIG. 1. As previously mentioned, the programmable temperature vaporizer 11 includes the sample unit 12, the temperature module 16 and the split ratio module 18. The sample unit 12 includes a sample chamber 38, and an inlet port 40, which can include a septum 41. The sample unit 12 further includes a carrier gas control valve 42, a carrier gas flow line 44, a flow rate sensor 46, a purge flow line 48 and a pressure sensor 50. The temperature module 16 includes a temperature sensor 52, a cooling device and a heater 54. The split ratio module 18 includes a split control valve 56 and a split flow line 58.

The inlet port 40, containing the septum 41, serves as an opening to insert the sample into the sample chamber 38. A carrier gas, such as nitrogen, flows along the carrier gas flow line 44 and into the sample chamber 38, and entrains the sample towards the analyzer 20 (shown in FIG. 1). The carrier gas control valve 42 controls the flow rate of carrier gas into the sample chamber 38. The flow rate sensor 46 measures the flow rate of the carrier gas. In one embodiment, the flow rate sensor 46 obtains the flow rate of the carrier gas by measuring the pressure at the inlet port 40 and calculates the corresponding flow rate.

Preferably, the carrier gas is an inert gas that does not react with any component of the system 10. For example, oxygen can have deleterious effects because of its oxidizing capabilities and might therefore be avoided. Consequently, the front end of the system 10, i.e., the sample unit 12, the temperature module 16, and/or the connector device 21 can be substantially closed to atmospheric air.

The purge flow line 48 allows for the removal of unwanted vapors that "bleed" out from the septum 41 during an analysis. The pressure sensor 50 measures the gas pressure of the purge flow line 48 to ensure that the purge flow rate remains within appropriate limits.

The temperature sensor 52 measures the temperature of the sample chamber 38. The cooling device 53 and heating device 54 change the temperature of the sample chamber 38 according to temperature instructions received from and determined by the controller 24. Alternatively, temperature instructions can be input by a user directly with the input device 22. For example, the cooling device 53 can use a nitrogen gas at 40–50 psi to cool the sample chamber 38, and the heating device 54 can be a resistive heating device.

The split control valve 56 controls the amount of sample gas vented through the vent 14 via the split flow line 58. The split control valve 56 can increase or decrease the amount of gas vented according to split ratio instructions received from and determined by the controller 24. Alternatively, the split ratio information can be input directly by a user with the input device 22.

An autoloader 57 can be used to load the sample into the chamber 38 via the inlet port 40.

Figure 3:
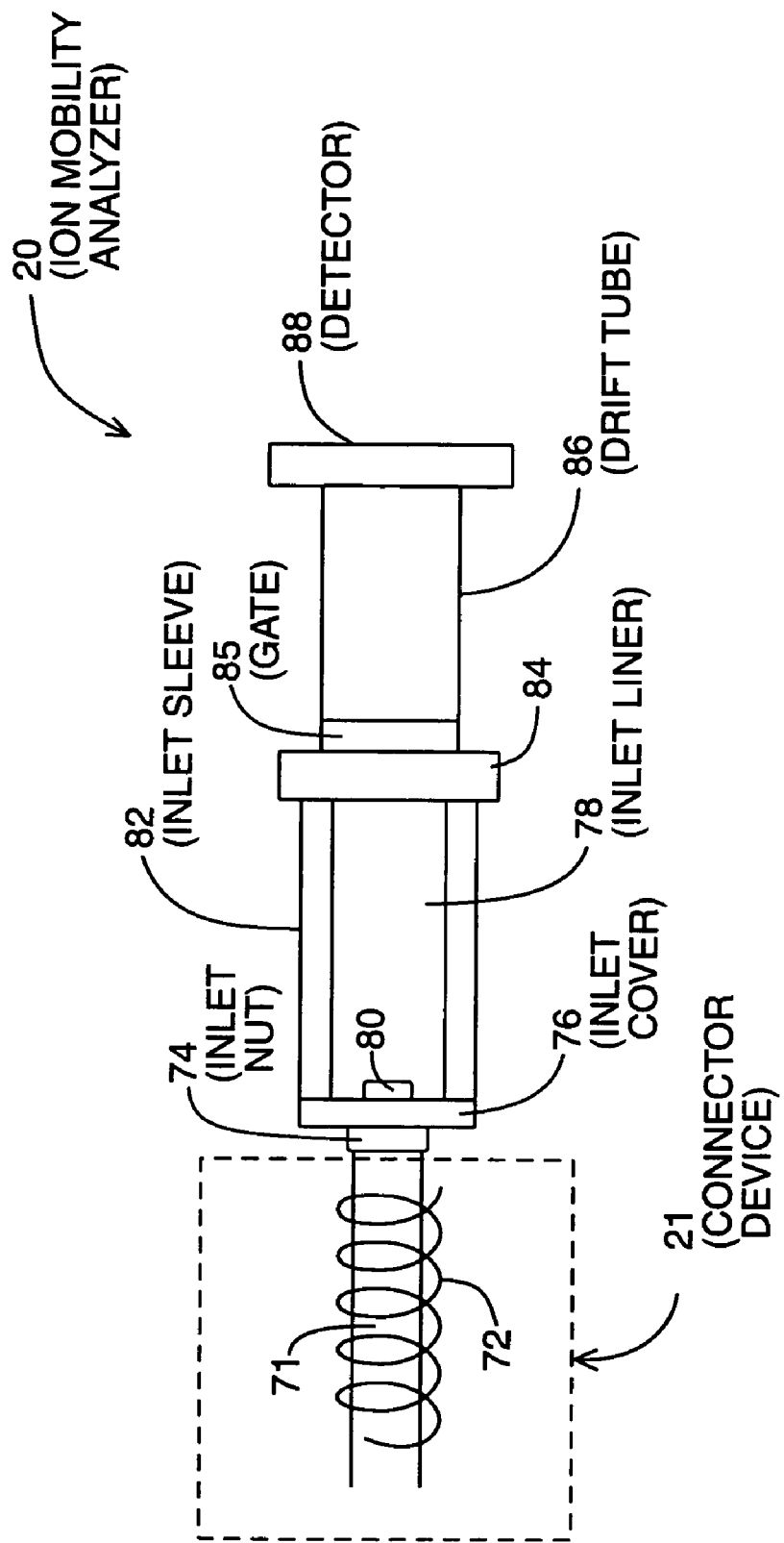
FIG. 3 shows a schematic diagram of the ion mobility analyzer and the connector device of FIG. 1.

FIG. 3 shows a schematic diagram of the ion mobility analyzer 20 and the connector device 21 of FIG. 1. The connector device 21 includes a transfer line 71 and a heating coil 72. The ion mobility analyzer 20 includes an inlet nut 74, an inlet cover 76, an inlet liner 78, which contains an orifice 80, and an inlet sleeve 82. The ion mobility analyzer 20 further includes an ionizer 84, a gate 85, a drift tube 86 and a detector 88.

The transfer line 71 transfers analyte from the sample chamber 38 to the inlet liner 78 of the ion mobility analyzer 20. In one embodiment, the transfer line 71 is about 7 cm in length and composed of uncoated silica. The transfer line 71 is surrounded by a heating coil 72 to maintain the analyte at an appropriate temperature, for example 25–400° C., or more typically 250–300° C., while being transferred from the sample chamber 38 to the inlet liner 78. The inlet liner 78, which can be a glass liner, is surrounded by the inlet sleeve 82. The inlet liner 78 also contains the orifice 80 to allow the transfer line 71 to have access to the interior of the inlet liner 78. The inlet liner 78 can be accessed by removing the inlet cover 76, for maintenance or diagnosing problems.

A sample gas, such as air or nitrogen, is forced into the inlet liner 78 to entrain the analyte towards the ionizer 84 and the drift tube 86. The inlet nut 74 affixes the transfer line 71 in place. The ionizer 84 can include a radioactive source for ionizing the analyte. The electronic gate 85 between the ionizer 84 and the drift tube 86 is normally closed, but, periodically, the gate 85 is opened for a short period of time to admit a pulse of ions for analysis into the drift tube 86. The detector 88 detects ions that reach the far end of the drift tube 86. The mobilities of the analyte ions are determined by calculating drift velocities as ions move, under the influence of an electric field, through a gas at ambient pressure in the drift tube 86. The operation of the ionizer 84, drift tube 86 and detector 88 in ion mobility spectrometry is known to those of ordinary skill in the art, and therefore is not further described in detail.

In operation, the detector 88 sends a ready signal to the autoloader 57 (shown in FIG. 2) to prepare the sample. After the autoloader 57 receives the ready signal from the sample unit 12, the autoloader 57 injects the sample into the sample unit 12. As the autoloader 57 injects the sample, it sends a signal to the sample unit 12 to commence operation. Subsequently, the autoloader 57 enters a post injection delay time mode, which leaves the autoloader 57 in standby. Next, the detector 88 acquires ion mobility data from ion velocities measured in a drift tube at ambient pressure. The ion mobilities are characteristic for the analyte, and therefore, can be used to identify the analyte. In addition, the strength of the signal received by the detector 88 is indicative of the amount of analyte present in the sample.

The principles of the present invention improve the reproducibility of this quantitative determination. In addition, the control and variability of the temperature of the vaporizer, as taught by the present invention, permit a greater range of solvents, including solvents that are relatively less volatile, such as water and various alcohols.

Figure 4B:
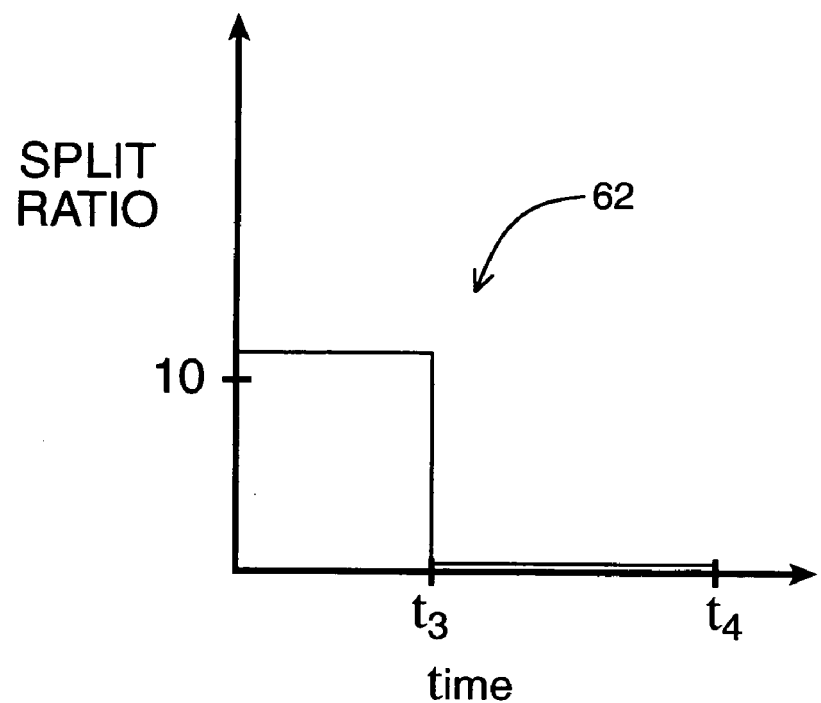
FIGS. 4A and 4B show plots of the temperature of the sample unit and the split ratio versus time in one embodiment of the present invention.
Figure 4A:
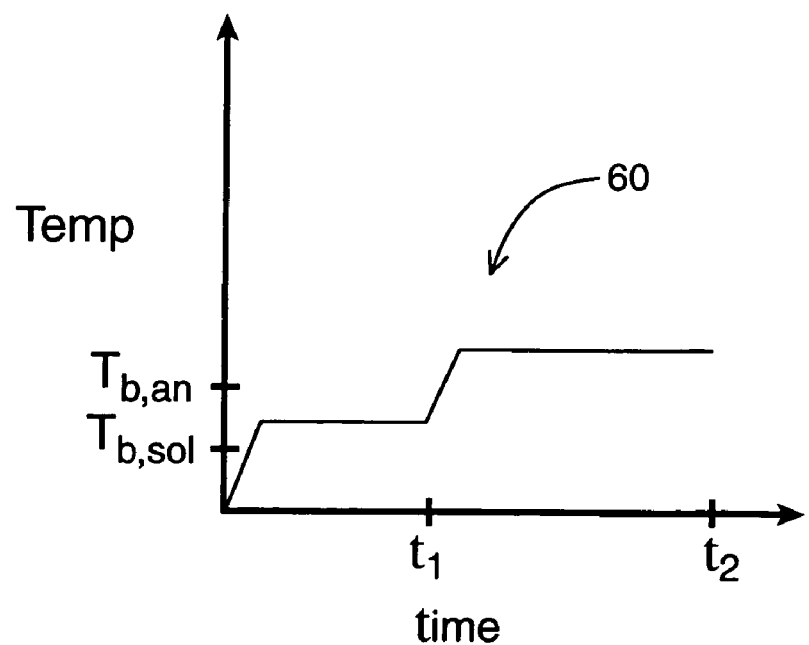

FIG. 4A shows a plot 60 of the temperature of the sample unit 12 versus time in one embodiment of the present invention. In a first stage, from time 0 to $t_1$, in which solvent is removed, the temperature module 16 raises and then substantially maintains the temperature of the sample unit 12 at a first temperature greater than the boiling point of the solvent, $T_{b,sol}$. In a second stage, from $t_1$ to $t_2$, in which analysis occurs, the temperature module 16 further raises and then substantially maintains the temperature of the sample unit 12 at a second temperature greater than the first temperature. The second temperature is typically greater than the boiling point of the analyte, $T_{b,an}$.

FIG. 4B shows a second plot 62 of the split ratio versus time. The split ratio module 18 maintains the split ratio within a first range during the first stage, from time 0 to $t_3$, and maintains the split ratio within a second range during the second stage, from $t_3$ to $t_4$. In one embodiment, the first range has values greater than or equal to values in the second range. Typically, the split ratio during the first stage is greater than ten, while the split ratio during the second stage is less than $10^{-2}$.

During the first stage, a sufficiently large portion of the solvent is vented through the vent 14. The duration of the first stage required for the discharge of the solvent is determined by the physical characteristics of the solvent and analyte, such as the boiling points of each. The duration also depends on the amount of sample to be inserted into the analyzer, different analyzers operating best with different sample sizes. It should be understood that the particular profiles of the plots 60 and 62 shown in FIGS. 4A and 4B are exemplary. Several other profiles of the plots 60 and 62 can also be employed. For example, the temperature during the first stage can be held at or near $T_{b,sol}$, and not necessarily above it. Additionally, the functional form of the plots in the first stage and second stage need not be linear. In another example, the split ratio can be maintained at zero during the entire analysis.

Figure 5B:
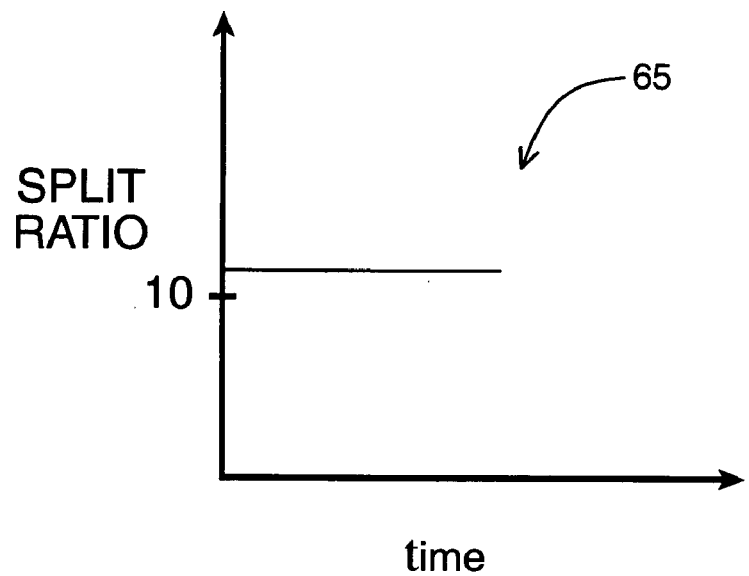
FIGS. 5A and 5B show plots of the temperature of the sample unit and the split ratio versus time in another embodiment of the present invention.
Figure 5A:
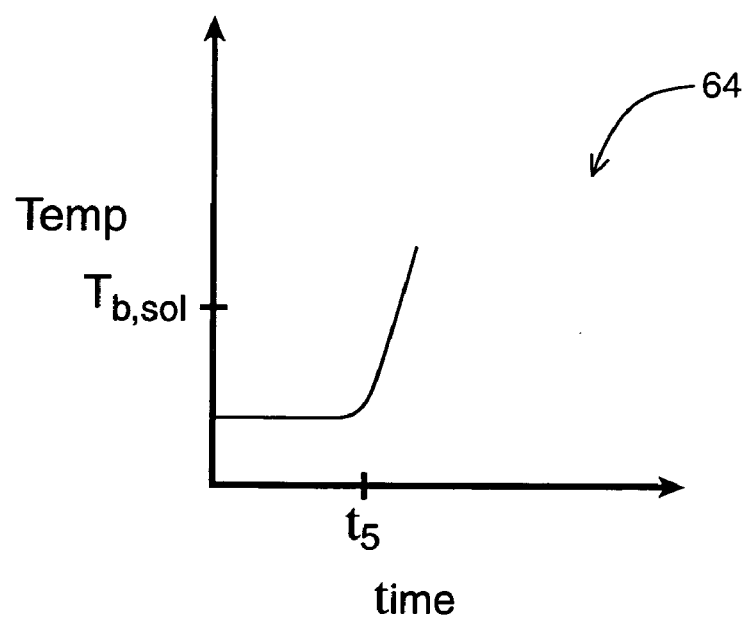

FIGS. 5A and 5B show another possible profile for the temperature and the split ratio, respectively. Plot 64 shows the temperature of the sample unit 12 versus time where the liquid sample is loaded into the inlet port 41 at a temperature below the boiling point of the solvent. The sample is evaporated under a flow of gas to vent the solvent. Then, at time $t_5$ the temperature is raised rapidly to vaporize the analyte. There may or may not be a delay between the loading of the sample and the rapid raising of the temperature. Plot 65 shows the split ratio versus time. The vent 14 is open for the entire analysis.

The principles of the present invention can be used when a sample contains several analyte components. In such case, more complicated profiles can be used to preferentially desorb each analyte component at successive desorption temperatures for subsequent analysis. Desorption temperature is a generalization of boiling temperature and refers to the temperature at which a significant amount of a substance is converted into a gas and entrained by a carrier gas into the analyzer. Under some conditions, an analyte component can begin to significantly desorb or evaporate at a temperature at or below the boiling point, such temperature being the desorption temperature. Thus, at the desorption temperature, enough analyte component is being removed from the sample to allow for an accurate measurement thereof using the ion mobility analyzer.

Suppose a sample contains a solvent and N analyte components $\{C_1, C_2, \ldots, C_N\}$, where component $C_i$ has a lower desorption temperature than $C_j$, if $i<j$, and the desorption temperature of the solvent is less than the desorption temperature of $c_1$. One possible profile that can be suitable under such conditions corresponds to a temperature that starts at some fixed value below the desorption temperature of the solvent. The temperature is then raised to a range that allows for the desorption or evaporation of the solvent. Alternatively, the initial temperature of the sample unit may be greater than the desorption temperature of the solvent but less than that of the component $c_1$. After a waiting period that can range from zero to some larger amount, the temperature is next further raised to at least the desorption temperature of $c_1$, but less than the desorption temperature of $c_2$. After a waiting period, which may be used to analyze component $c_1$, the temperature is raised to at least the desorption temperature of $c_2$, but less than the desorption temperature of $C_3$, and so on until the $C_N$ component has been desorbed. As each analyte component is desorbed, it is entrained by the carrier gas into the analyzer for analysis. In this manner, each component is analyzed separately, reducing the amount of interference present in the analysis. In addition, the split ratio of at least one member of the group consisting of the solvent and the N analyte components may be adjusted, according to split ratio instructions received by a split ratio module, as described above. Thus, the principles of the present invention provide a user with a more controlled desorption of analytes compared to uncontrolled heating for the introduction of the analyte into the ion mobility analyzer.

Where there is no solvent, or where the desorption temperature of the solvent is greater than that for $c_N$, the method can begin by adjusting the temperature to at least the desorption temperature of $c_1$, but less than the desorption temperature of $c_2$. After a waiting period, the temperature is adjusted to at least the desorption temperature of $c_2$, but less than the desorption temperature of $c_3$, and so on until the $C_N$ component has been desorbed. As each analyte component is desorbed, it is entrained by the carrier gas into the analyzer for analysis. In addition, the split ratio of at least one member of the group consisting of the N analyte components may be adjusted, according to split ratio instructions received by a split ratio module, as described above.

It should be noted that the timing of the split ratio module 18 is typically independent of the timing of the temperature module 16. However, in other embodiments, the timing of the split ratio module 18 can be dependent on the timing of the temperature module 16.

The heating reflected in the plot 60 enables large volume liquid sample introductions into the spectrometer 10 while increasing reproducibility and the number of solvents that can be employed.

In particular, because the presence of some solvents can alter the resulting plasmagram, by controlling the amount of volume entering the sample unit, greater reproducibility can be achieved. The present invention permits venting of the sample to remove solvent in a controllable and fast manner. Fast venting also implies that there is less time for other factors, such as ambient temperature and humidity to influence results.

Moreover, the principles of the present invention increase the reproducibility of the experimental results by substantially closing the front end of the system 10 to atmospheric gas, by using an inert carrier gas, and by controlling the temperature of the sample unit 12. These steps also maintain the integrity of both the inlet liner 78 and the programmable temperature vaporizer 11 surfaces, which also improve the reproducibility sensitivity of the system 10. The aforementioned features of the present invention also reduce both random and systematic error.

In addition, the present invention can increase the effective dynamic range, which refers to the range of amount or concentration of analyte that can be meaningfully measured. If this amount or concentration is beyond a maximum limit, saturation of the signal occurs where a further increase in analyte results in little or no change in the measured signal characteristic of the analyte. An initial volume of solution containing an amount of analyte that is outside the dynamic range can still be used if the teachings of the principles of the present invention are employed. By splitting the volume to bring the amount of analyte down to a level within the dynamic range, larger volumes of sample can be used, effectively increasing the dynamic range of the system 10.

It should be understood that various modifications and adaptations could be made to the embodiments described and illustrated herein, without departing from the present invention. For example, although temperature and split ratio curve profiles have been discussed that are substantially piece-wise constant, various other profiles can be used that are appropriate to the sample being analyzed. In particular, non-linear functional forms for the profiles can be used. Moreover, although samples in the form of a solution of an analyte and a solvent are described above, it should be understood that the sample might be introduced into the sample unit 12 without a solvent. A solid sample of analyte, for example, can be introduced and then vaporized. The analyte may also be introduced into the sample unit as a gas or liquid provided the sample is capable of being vaporized. It should also be understood that not just one, but also several components within a sample could be advantageously analyzed using the principles of the present invention. The scope of the invention is to be defined in the appended claims.

What is claimed is:

1. An ion mobility spectrometer for analyzing a sample containing an analyte, the ion mobility spectrometer comprising
    a sample unit for holding the sample, said sample unit including a vent;
    a temperature module for adjusting temperature of the sample unit according to temperature instructions received;
    an ion mobility analyzer for determining an ion mobility of the analyte received from the sample unit;
    a connector device for connecting and transferring the analyte from the sample unit to the ion mobility analyzer, the ion mobility being used to characterize the sample; and
    a split ratio module for adjusting a split ratio according to split ratio instructions received, the split ratio characteristic of the ratio of the flow rate of gas discharged through the vent to the flow rate of gas being delivered to the ion mobility analyzer from the sample unit.

2. The system of claim 1, wherein the sample also includes a solvent.

3. The system of claim 2, further comprising an input device for inputting the temperature instructions and the split ratio instructions.

4. The system of claim 2, further comprising a controller for sending the temperature instructions to the temperature module and the split ratio instructions to the split ratio module.

5. The system of claim 4, wherein the controller determines the temperature instructions and the split ratio instructions based on physical characteristics of the sample.

6. The system of claim 2, wherein the temperature module increases the temperature of the sample unit after the sample is introduced thereto to vaporize the sample.

7. The system of claim 2, wherein the temperature module, in a first stage, raises and then substantially maintains the temperature of the sample unit at a first temperature above the boiling point of the solvent, and, in a second stage, further raises and then substantially maintains the temperature of the sample unit at a second temperature greater than the first temperature.

8. The system of claim 7, wherein the second temperature is greater than the boiling point of the analyte.

9. The system of claim 8, wherein the split ratio module maintains the split ratio within a first range during the first stage and maintains the split ratio within a second range during the second stage, the first range having values greater than or equal to values in the second range.

10. The system of claim 9, wherein the split ratio during the first stage is greater than ten.

11. The system of claim 10, wherein the split ratio during the second stage is less than $10^{-2}$.

12. The system of claim 2, wherein the sample unit includes
    a sample chamber for containing the sample while the temperature module heats the sample therein;
    an inlet port having a septum for allowing the sample to enter the sample chamber;
    a carrier gas flow line for allowing a carrier gas to flow into the sample chamber to entrain the sample from the sample chamber to the analyzer;
    a flow rate sensor for measuring the flow rate of carrier gas in the carrier gas flow line; and
    a carrier gas control valve for controlling the flow of the carrier gas into the sample chamber.

13. The system of claim 12, wherein the sample unit further includes a purge flow line for the removal of unwanted vapors that bleed out from the septum.

14. The system of claim 2, wherein atmospheric air is prevented from entering at least one of the sample unit, the temperature module and the connector device.

15. The system of claim 2, wherein the system is closed to prevent atmospheric air to enter therein.

16. A method for analyzing a sample containing an analyte with an ion mobility analyzer, the method comprising
holding a sample in a sample unit containing the analyte, said sample unit including a vent;
adjusting a temperature of the sample unit according to temperature instructions received by a temperature module;
adjusting a split ratio according to split ratio instructions received by a split ratio module, the split ratio characteristic of the ratio of the flow rate of gas discharged through the vent to the flow rate of gas being delivered to the ion mobility analyzer from the sample unit; and
transferring the analyte from the sample unit to the ion mobility analyzer.

17. The method of claim 16, further comprising determining an ion mobility of the analyte received from the sample unit with an ion mobility analyzer, the ion mobility being used to characterize the sample.

18. The method of claim 17, wherein the sample also contains a solvent.

19. The method claim 18, further comprising inputting the temperature instructions and the split ratio instructions with an input device.

20. The method of claim 18, further comprising
sending the temperature instructions to the temperature module by the controller; and
sending split ratio instructions to the split ratio module by the controller.

21. The method of claim 20, further comprising
the controller determining the temperature instructions; and
the controller determining the split ratio instructions based on physical characteristics of the sample.

22. The method of claim 18, wherein the temperature of the sample unit is raised by the temperature module after the sample is introduced in the sample unit to vaporize the sample.

23. The method of claim 18, further comprising
in a first stage, the temperature module raising and then substantially maintaining the temperature of the sample unit at a first temperature above the boiling point of the solvent; and
in a second stage, the temperature module further raising and then substantially maintaining the temperature of the sample unit at a second temperature greater than the first temperature.

24. The method of claim 23, wherein, in the step of further raising, the second temperature is greater than the boiling point of the analyte.

25. The method of claim 24, further comprising
the split ratio module maintaining the split ratio within a first range during the first stage; and
the split ratio module maintaining the split ratio within a second range during the second stage, the first range having values greater than or equal to values in the second range.

26. The method of claim 25, wherein, in the step of maintaining the split ratio within a first range, the split ratio during the first stage is greater than ten.

27. The method of claim 26, wherein, in the step of maintaining the split ratio within a second range, the split ratio during the second stage is less than $10^{-2}$.

28. The method of claim 18, further comprising
containing the sample in a sample chamber while the temperature module heats the sample therein; and
allowing the sample to enter the sample chamber via an inlet port having a septum;
allowing a carrier gas to flow through a carrier gas flow line and into the sample chamber to entrain the sample from the sample chamber to the analyzer;
measuring the flow rate of carrier gas in the carrier gas flow line; and
controlling the flow of the carrier gas into the sample chamber.

29. The method of claim 28, further comprising removing unwanted vapors that bleed out from the septum.

30. The method of claim 18, wherein in the step of transferring, the analyte is transferred from the sample unit to the ion mobility analyzer via a connector device, the method further comprising preventing atmospheric gas from entering at least one of the sample unit, the temperature module and the connector device.

31. A method for analyzing with an ion mobility analyzer a sample containing N analyte components, $[C_1 C_2 \ldots, C_N]$, the method comprising holding the sample in a sample unit; adjusting the temperature of the sample unit to at least that of the desorption temperature of $c_1$, to allow desorption thereof; transferring $c_1$ from the sample unit to the ion mobility analyzer for analysis; adjusting the temperature of the sample unit to at least that of the desorption temperature of $c_2$ to allow desorption thereof; transferring $c_2$ from the sample unit to the ion mobility analyzer for analysis; and where N>2, repeating the steps of adjusting and transferring until all N components are transferred to the ion mobility analyzer for analysis, wherein N is an integer greater than one, and component $C_i$ has a lower desorption temperature than $C_j$ if i<j, and wherein the sample unit has a vent, further comprising adjusting a split ratio of at least one member of the group consisting of the N components, according to split ratio instructions received by a split ratio module, the split ratio characteristic of the ratio of the flow rate of gas discharged through the vent to the flow rate of gas being delivered to the ion mobility analyzer from the sample unit.

32. The method of claim 31, wherein at least one of the N analyte components is dissolved in a solvent and wherein the desorption temperature of the solvent is less than the desorption temperature of $c_1$, the method further comprising
before the step of adjusting the temperature of the sample unit to at least that of the desorption temperature of $c_1$, adjusting the temperature of the sample unit to at least the desorption temperature of the solvent to allow desorption thereof.

33. The method of claim 32, wherein the sample unit has a vent, further comprising adjusting a split ratio of at least one member of the group consisting of the solvent and the N components, according to split ratio instructions received by a split ratio module, the split ratio characteristic of the ratio of the flow rate of gas discharged through the vent to the flow rate of gas being delivered to the ion mobility analyzer from the sample unit.

34. The method of claim 31, further comprising determining with an ion mobility analyzer an ion mobility of at least one of the N analyte components received from the sample unit, the ion mobility being used to characterize the sample.

35. The method of claim 33, further comprising determining with an ion mobility analyzer an ion mobility of at least one of the N analyte components received from the sample unit, the ion mobility being used to characterize the sample.

* * * * *